(12) United States Patent
Bontus et al.

(10) Patent No.: US 11,890,127 B2
(45) Date of Patent: Feb. 6, 2024

(54) ADAPTIVE HELICAL COMPUTED TOMOGRAPHY

(71) Applicant: KONINKLIJKE PHILIPS N.V., Eindhoven (NL)

(72) Inventors: Claas Bontus, Hamburg (DE); Holger Schmitt, Luetjensee (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 17/419,786

(22) PCT Filed: Jan. 6, 2020

(86) PCT No.: PCT/EP2020/050112
§ 371 (c)(1),
(2) Date: Jun. 30, 2021

(87) PCT Pub. No.: WO2020/144124
PCT Pub. Date: Jul. 16, 2020

(65) Prior Publication Data
US 2022/0071586 A1    Mar. 10, 2022

(30) Foreign Application Priority Data
Jan. 9, 2019 (EP) .................................. 19150983

(51) Int. Cl.
*A61B 6/00* (2006.01)
*A61B 6/02* (2006.01)
(Continued)

(52) U.S. Cl.
CPC .............. *A61B 6/545* (2013.01); *A61B 6/027* (2013.01); *A61B 6/032* (2013.01); *A61B 6/0407* (2013.01);
(Continued)

(58) Field of Classification Search
CPC .... A61B 6/00; A61B 6/03; A61B 6/04; A61B 6/06; A61B 6/02; A61B 6/545;
(Continued)

(56) References Cited

U.S. PATENT DOCUMENTS

| 7,187,745 B2 | 3/2007 | Flohr et al. |
| 7,515,678 B2 | 4/2009 | Hsieh |

(Continued)

FOREIGN PATENT DOCUMENTS

| JP | 2006311882 A | 11/2006 |
| WO | WO2006090321 A1 | 8/2006 |

OTHER PUBLICATIONS

PCT International Search Report, International application No. PCT/EP2020050112, dated Mar. 9, 2020.

*Primary Examiner* — Jurie Yun
(74) *Attorney, Agent, or Firm* — Larry Liberchuk (57) ABSTRACT

A device (10) for controlling an image acquisition of a multi-slice computed tomography system (1), MSCT, is disclosed. The device comprises an input (11) for receiving projection image data from the MSCT (1), an output (12) for controlling operation of the MSCT (1) and a processor (13). The processor (13) is adapted for controlling the MSCT to acquire a large volume localizer radiograph, and for defining an organ region in the localizer radiograph that delimits an organ of interest. The processor is adapted for acquiring a large volume helical CT scan of the subject, in which an X-ray cone angle is increased when the organ region in the subject is translated into the examination volume and decreased when the organ region is translated out of the examination volume.

15 Claims, 2 Drawing Sheets

(51) Int. Cl.
*A61B 6/03* (2006.01)
*A61B 6/04* (2006.01)
*A61B 6/06* (2006.01)

(52) U.S. Cl.
CPC ............... *A61B 6/06* (2013.01); *A61B 6/405* (2013.01); *A61B 6/4085* (2013.01); *A61B 6/4233* (2013.01); *A61B 6/4435* (2013.01)

(58) Field of Classification Search
CPC ..... A61B 6/032; A61B 6/0407; A61B 6/4085; A61B 6/027; A61B 6/4435; A61B 6/405; A61B 6/4233; A61B 6/481; A61B 6/503; A61B 6/5211; A61B 6/542; A61B 6/488
See application file for complete search history.

(56) References Cited

U.S. PATENT DOCUMENTS

| | | |
|---|---|---|
| 7,680,313 B2 | 3/2010 | Gundel |
| 9,320,480 B2 | 4/2016 | Gorges et al. |
| 2004/0202283 A1 | 10/2004 | Okumura |
| 2006/0203966 A1 | 9/2006 | Mollus |
| 2006/0262896 A1 | 11/2006 | Nishide |
| 2009/0274265 A1 | 11/2009 | Koehler et al. |
| 2012/0128120 A1 | 5/2012 | De Man |
| 2015/0173692 A1 | 6/2015 | Heuscher |
| 2018/0070908 A1 | 3/2018 | Netabayashi |

ADAPTIVE HELICAL COMPUTED TOMOGRAPHY

FIELD OF THE INVENTION

The invention relates to the field of multi-slice helical computed tomography, e.g. to computed tomography systems comprising a multiple-row detector array and configured for helical scanning of a subject. More specifically it relates to a device for controlling an image acquisition of a multi-slice computed tomography system, a multi-slice computed tomography system and a related method.

BACKGROUND OF THE INVENTION

It is known in the art that a large coverage in computed tomography, e.g. as provided by a detector array comprising many detector rows, can be advantageous. For example, an entire organ, e.g. the heart, can be covered simultaneously in an X-ray cone during the acquisition of projection data for tomographic reconstruction. The length of a longitudinal segment of the body that can be covered simultaneously when acquiring projection data can be advantageously increased, e.g. up to 16 cm, such that axial scans can be obtained having a good spatial as well as temporal resolution. This coverage is typically increased by increasing the number of detector rows in the computed tomography system, such that both a high spatial resolution as well as a large coverage can be provided.

Helical computed tomography acquisition is known in the art as an efficient and fast approach to obtain radiographic projection data that can be reconstructed into a qualitative three-dimensional image covering a large volume of the imaged subject, e.g. a scan of a whole or a substantial part of a body.

However, for helical scanning, the X-ray cone is typically collimated such that only parts of the detector get illuminated, e.g. the number of detector rows which are used for the helical scan may be less than the available number of rows. Furthermore, since the subject is scanned along a longitudinal axis in such helical scan, the temporal resolution of the helical scan may be rather low, e.g. motion artefacts may be present in the acquired volumetric image.

Various applications, such as trauma cases, may require both a large volume overview, e.g. a whole-body scan or a scan of a substantial part of the body, as well as high temporal and/or spatial resolution reconstructed images for a more limited region of interest, such as an organ of interest, such as the heart.

US 20060262896 discloses a method in which a scout image of a subject is displayed. An operator designates at least one range in a body-axis direction, of the scout image. Further, the operator graphically inputs or key-inputs and sets imaging condition parameters such as a helical pitch, a noise index and the like for a shuttle mode helical scan with being made independent every ranges. Thus, conditions such as helical pitch and noise index for the shuttle mode helical scan can efficiently and intelligibly be set independently for each region or organ, which allows for an optimization and detailed control of the imaging conditions.

US2015/173692A1 discloses a CT device with a dynamic collimator which defines an aperture adjustable to permit radiation to pass through the volume of interest.

WO2006/090321 discloses a CT apparatus which uses a low radiation dose during a scan of a relatively large portion in which an organ of the human being is expected to detect an object of interest, and a second scan of a more limited portion of the object of interest with an increased radiation dose.

US2004/202283 discloses a CT apparatus including an X-ray irradiation source, an X-ray detector including a plurality of detection element segments, and a collimator configured to create an opening that is movable in at least one of a slice direction and a channel direction and a controller configured to perform a first and second helical scan. In the first scan, the helical pitch and the opening of the collimator in the channel direction are selected rather large for a fast low-resolution scan. In a second scan, the collimator and helical pitch are selected rater limited for a high-resolution scan.

US2018/070908 discloses a CT apparatus for performing a first scan of an object, identifying a shape of an anatomical site of the object based on the shape of the anatomical site, and performing a second scan which is a tilt scan in which the rotating body of the CT apparatus is tilted.

SUMMARY OF THE INVENTION

It is an object of embodiments of the present invention to provide good, efficient and fast means and methods for scanning a subject using a multi-slice computed tomography system.

It is an advantage of embodiments of the present invention that a large volume of a subject can be scanned, e.g. in a scan of a whole body or a substantial part of a body, such that an overview tomographic reconstruction can be performed, while concurrently collecting data to enable a further tomographic reconstruction of an organ of interest.

It is an advantage of embodiments of the present invention that motion artefacts in a tomographic reconstruction of a highly mobile organ can be avoided or reduced. It is an advantage of embodiments of the present invention that the temporal and/or spatial resolution of the further tomographic reconstruction of the organ of interest can be higher than the overview tomographic reconstruction.

It is an advantage of embodiments of the present invention that both an overview, e.g. a scan of a full body or a substantial part of the body, and a high temporal resolution scan of an organ of interest, e.g. a scan of the heart within a single heart beat, can be obtained in a single operation.

It is a further advantage that such integrated scan procedure can be performed quickly, for example offering advantages in fast trauma response and operational efficiency. It is a further advantage that such integrated scan procedure can be performed without relying on an operator to manually define a volume corresponding to the organ of interest, thus avoiding a delay and a decrease in efficiency due to such reliance on a user.

It is an advantage of embodiments of the present invention that a constant table feed can be maintained. It is an advantage that motion artefacts due to acceleration and/or deceleration during the operation can be avoided. It is a further advantage that a risk to the subject implied by acceleration and/or deceleration can be reduced, e.g. in a trauma case. It is a further advantage that the comfort for the subject can be increased by avoiding sudden and/or frequent changes in translation velocity.

The above object is accomplished by a method and device according to the present invention.

In a first aspect the present invention relates to a device for controlling an image acquisition of a multi-slice computed tomography system comprising a rotatable gantry), a multi-row detector, an X-ray source and an automated examination couch moving in a longitudinal direction. The device comprises an input for receiving projection image data from the multi-row detector of the multi-slice computed tomography system and an output for controlling operation of the multi-slice computed tomography system. The device also comprises a processor.

The processor is adapted for controlling a first operation of the multi-slice computed tomography system via the output so that a large volume computed tomography localizer radiograph of a subject to be imaged is acquired. The processor is adapted for receiving the computed tomography localizer radiograph via the input.

The processor is adapted for controlling a second operation of the computed tomography system via the output so that a large volume helical computed tomography scan of the subject is acquired, in which the subject is translated by the automated examination couch through an examination volume, e.g. circumscribed by the rotating gantry.

Controlling the second operation comprises increasing an X-ray cone angle of the computed tomography system in the longitudinal direction when the translation of the subject by the automated examination couch causes an organ region, which is defined on the computed tomography localizer radiograph and substantially delimits an organ of interest in the subject, to enter into the examination volume, e.g. from an outer boundary of the organ region up to a center line of the organ region, and decreasing the X-ray cone angle when the translation of the subject causes the organ region to leave the examination volume, e.g. from the center line of the organ region up to an outer boundary of the organ region.

In a device in accordance with embodiments of the present invention, the processor may be adapted for receiving the computed tomography localizer radiograph via the input and for detecting the organ region in the computed tomography localizer radiograph that substantially delimits an organ of interest, e.g. a heart, in the subject.

In a device in accordance with embodiments of the present invention, the processor may be adapted for controlling an aperture of a controllable collimator of the computed tomography system to increase and decrease the X-ray cone angle.

In a device in accordance with embodiments of the present invention, the processor may be adapted for fitting a model of the organ of interest on the computed tomography localizer radiograph.

In a device in accordance with embodiments of the present invention, the model may comprise a representative image of the organ and the fitting may comprise applying an image registration algorithm.

In a device in accordance with embodiments of the present invention, the model may comprise a representative parametric model of the organ and the fitting may comprise estimating parameters of the model such as to conform with the computed tomography localizer radiograph.

In a device in accordance with embodiments of the present invention, the model may be a two-dimensional model indicative of a projection view, of the organ of interest, that corresponds to the computed tomography localizer radiograph projection.

In a device in accordance with embodiments of the present invention, the model may be a three-dimensional model of the organ of interest.

In a device in accordance with embodiments of the present invention, the processor may be adapted for detecting the organ region by determining a lower bound, an upper bound and a center position of the organ in a longitudinal direction corresponding to the direction of translation of the examination couch.

In a device in accordance with embodiments of the present invention, the processor may be adapted for increasing the X-ray cone angle when the upper bound of the detected organ region coincides with the examination region, and decreasing the X-ray cone angle when the lower bound of the detected organ region coincides with the examination region. For example, by increasing the X-ray cone angle, the number of detector rows on which radiation from the X-ray source impinges during the operation may be increased, and likewise the number of active detector rows may be decreased by decreasing the X-ray cone angle.

In a device in accordance with embodiments of the present invention, the processor may be adapted to receive an electrophysiological signal, e.g. an ECG signal, in which this signal is acquired concomitantly, e.g. simultaneously, with the scan of the second operation. The processor may be adapted for determining the number of projections that are acquired, with the enlarged X-ray cone angle, for each of a plurality of heart beat phases. For example, when a predetermined minimum number of projections are acquired for each phase, the cone angle may be decreased, e.g. even before the lower bound such as mentioned hereinabove is reached.

In a device in accordance with embodiments of the present invention, the processor may be adapted for increasing and decreasing the X-ray cone angle by a substantially continuous transition, e.g. respectively a linear increase and a linear decrease.

In a device in accordance with embodiments of the present invention, controlling the second operation may comprise increasing an X-ray tube current of the computed tomography system when the translation of the subject by the automated examination couch causes the organ region to enter into the examination volume and decreasing the X-ray tube current when the translation of the subject causes the organ region to leave the examination volume.

In a device in accordance with embodiments of the present invention, the processor may be adapted for controlling a translation velocity of the automated examination couch such as to remain substantially constant during said second operation.

A device in accordance with embodiments of the present invention may be, or may be comprised in, an operator console system for controlling the multi-slice computed tomography system.

A device in accordance with embodiments of the present invention may comprise a further output for controlling a contrast agent administration device for introducing a contrast agent in the body of the subject. The processor may be adapted for sending a control signal via the further output to administer the contrast agent to the subject when, or at a predetermined time interval before, the translation of the subject by the automated examination couch causes the organ region to enter into the examination volume.

In a second aspect, the present invention relates to a multi-slice computed tomography system comprising a device in accordance with embodiments of the first aspect of the present invention.

In a third aspect, the present invention relates to a method for controlling a multi-slice computed tomography system comprising an X-ray source, a multi-row detector and an automated examination couch moving in a longitudinal direction. The method comprises acquiring a large volume computed tomography localizer radiograph of a subject to be imaged using the multi-slice computed tomography system, defining an organ region in the large volume computed tomography localizer radiograph, in which the organ region substantially delimits an organ of interest in the subject, and acquiring a large volume helical computed tomography scan of the subject, in which the subject is translated by an automated examination couch through an examination volume. The method also comprises increasing an X-ray cone angle, and optionally also an X-ray tube current, of the computed tomography system in the longitudinal direction when the translation of the subject by the automated examination couch during the helical computed tomography scan causes the organ region to enter into an examination volume of the multi-slice computed tomography system and decreasing the X-ray cone angle in the longitudinal direction, and optionally also the X-ray tube current, when the translation of the subject during the helical computed tomography scan causes the organ region to leave the examination volume.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a device for controlling an image acquisition of a multi-slice computed tomography (CT) system, e.g. a multi-slice computed tomography system in accordance with embodiments of the second aspect of the present invention.

Figure 1:
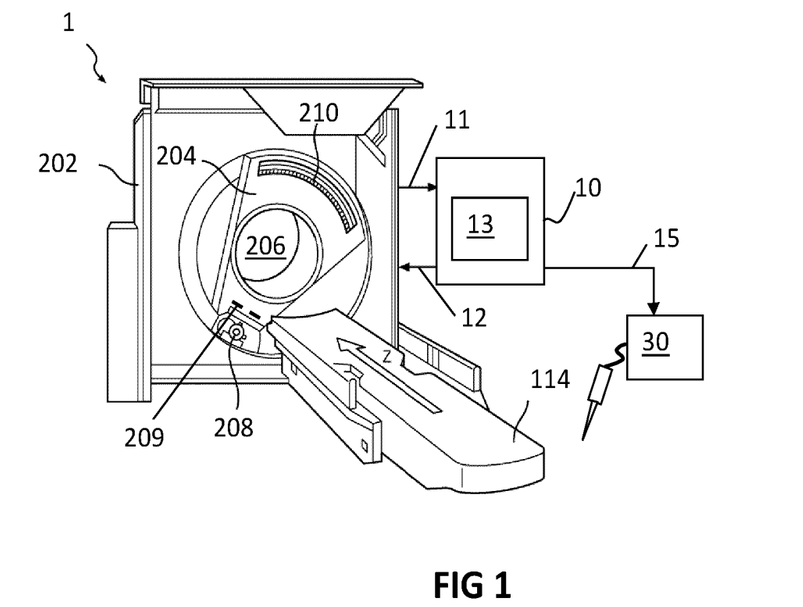
FIG. 1 illustrates a device and a method in accordance with embodiments of the present invention.

In FIG. 1, a device 10 in accordance with embodiments of the first aspect of the present invention is shown, as well as a multi-slice computed tomography system 1 in accordance with embodiments of the second aspect of the present invention.

The device 10 may be, or may be comprised in, a console system for controlling the multi-slice computed tomography system 1.

The device 10 comprises an input 11 for receiving projection image data (and optionally other status data, such as couch position and/or motion information, gantry operation information, electrophysiological information, e.g. an ECG signal, X-ray tube status information and/or detector status information) from a multi-row detector of the multi-slice computed tomography system 1 and an output 12 for controlling the operation of the multi-slice computed tomography system 1.

The device 10 further comprises a processor 13 adapted for controlling a first operation of the CT system 1, via the output 12, such that a CT localizer radiograph of a subject to be imaged is acquired. A CT localizer radiograph is, as known in the art, a scanned projection radiograph, e.g. acquired while translating the subject through the CT gantry using an automated examination couch while the gantry remains in a stationary position, which is often acquired to enable an operator to prescribe the start and end positions of a scan range. Other common terms referring to such CT localizer radiograph include scout scan, surview, topogram and scanogram. For example, the CT localizer radiograph may be a two-dimensional projection image of the subject to be imaged, e.g. while positioned on the automated examination couch, for example a frontal radiographic projection image, e.g. an anteroposterior or posteroanterior image.

The processor 13 is adapted for receiving the CT localizer radiograph via the input 11.

The processor 13 may be adapted for detecting an organ region in the CT localizer radiograph such that the organ region substantially delimits an organ of interest in the subject.

Alternatively the edges, or at least two opposite extreme boundaries in the longitudinal direction, of the organ can be determined by human visual inspection based on the localizer radiograph, e.g. selected using a graphical user interface, such as to determine the organ region that substantially delimits the organ of interest in the subject.

Substantially delimits may refer to defining at least approximately, e.g. within a margin of accuracy, e.g. of up to 10 cm, preferably, up to 5 cm, e.g. even more preferred within 1 cm accuracy, at least a lower bound and an upper bound of the organ in the longitudinal direction corresponding to the direction of translation of the examination couch. Furthermore, the processor may be adapted for determining a center position of the organ in between the lower bound and the upper bound, e.g. the average of lower bound and the upper bound.

In an exemplary embodiment, the organ of interest may be a heart. However, in other embodiments, the organ may be a lung or the lungs, a liver, a stomach, a spleen, a pancreas, a part or parts of the gastrointestinal tract, a kidney or the kidneys, a uterus, a brain, etc. In particularly advantageous embodiments, the organ is characterized by a function that implies frequent motion, e.g. a local displacement of at least some part thereof over a distance of at least a millimeter, e.g. at least a centimeter, within a time frame of 5 s or less, e.g. of 1 s or less, such as the heart or the lungs.

The processor 13 may be adapted for fitting a model of the organ of interest on the CT localizer radiograph. For example, the model may comprise a representative image of the organ, and the fitting may comprise applying an image registration algorithm, e.g. a rigid, an affine or a deformable registration. For example, the model may comprise a representative parametric model of the organ, and the fitting may comprise estimating parameters of the model such as to conform with the CT localizer radiograph. The parameters may comprise spatial parameters, such as a 2D or 3D position, an orientation, such as a 2D or 3D angle, scale parameters, e.g. a 1D, 2D or 3D scaling, skewing parameters, and/or other parameters indicative of anatomical variations amongst different subjects. The model may also comprise other body parts such as to fit the organ of interest within the context of surrounding body structures.

The fitting may comprise fitting a two-dimensional model, e.g. a reference image or parametric model, on the two-dimensional CT localizer radiograph. For example, suitable algorithms for 2D/2D registration are well-known in the art.

The fitting may also comprise fitting a three-dimensional model, e.g. a reference volumetric image or parametric model, on the two-dimensional CT localizer radiograph. For example, suitable algorithms for 2D/3D registration are known in the art, e.g. for registration of pre- and intra-interventional data for image-guided radiation therapy, radiosurgery, endoscopy and/or interventional radiology.

For example, the location of the organ of interest, such as the heart, may be approximately determined in the CT localizer radiograph. This can be done, for example, by registering the edges of a model of the organ, e.g. of a heart model, with the intensity gradients in the localizer radiograph image. The center position of the organ can then also be easily determined, e.g. in the middle of the cranial and caudal edge of the registered organ model.

The processor 13 is further adapted for controlling a second operation of the CT system, via the output 12, such that a helical CT scan of the subject is acquired, in which a rotation of the gantry and a translation of the examination couch are controlled to obtain a helical CT scan, e.g. at a first pitch.

Controlling this second operation comprises increasing an X-ray cone angle of the CT system, e.g. by enlarging the aperture provided by a controllable collimator, when the translation of the subject by the automated examination couch causes the organ region to enter into the examination volume defined by the gantry, and decreasing the X-ray cone angle of the CT system when the translation of the subject by the automated examination couch causes the organ region to leave the examination volume, e.g. so that the organ region is scanned at a second pitch smaller than the first pitch.

For example, the X-ray cone angle may be increased when the upper bound of the organ region coincides with the examination volume, and the X-ray cone angle may be decreased when the lower bound of the organ region coincides with the examination volume. In the present disclosure, the 'upper' and 'lower' bound do not necessarily correspond to anatomical posterior and inferior aspects of the organ of interest, but may be defined in terms of the sense of translation of the subject through the examination volume defined (e.g. circumscribed) by the gantry during the second operation. For example, the upper bound may correspond to a superior boundary of the organ and the lower bound may correspond to an inferior boundary of the organ when the subject is translated in an inferior to posterior sense, but the upper bound may correspond to an inferior boundary of the organ and the lower bound may correspond to a superior boundary of the organ when the subject is translated in a posterior to inferior sense of direction.

Alternatively, if the organ is the heart, the region along which data are measured with large cone angle may be related to a measured ECG signal.

The X-ray cone angle may be increased and decreased by a discrete step, e.g. from a narrow cone, e.g. used for a helical scan of a full body or a substantial part of a body, to a wide cone, e.g. suitable for reconstructing a tomographic image of the organ at a high(er) temporal and/or spatial resolution, and back to the narrow cone.

Preferably, the X-ray cone angle may be increased and decreased by a continuous (or substantially continuous, e.g. in a plurality of smaller discrete steps) transition. For example, the cone angle may be increased from the narrow cone to the wide cone by a (substantially) continuous increasing function (of time or position), e.g. a linear increase, in between the upper bound and the center position of the organ, and decreased from the wide cone to the narrow cone by a (substantially) continuous decreasing function (of time or position), e.g. a linear decrease, in between the center position of the organ and the lower bound.

Preferably, the X-ray tube current may be increased when the upper bound of the organ region coincides with the examination volume, and the X-ray tube intensity may be decreased when the lower bound of the organ region coincides with the examination volume. Similar to the description hereinabove, such increase and decrease of the tube current may be performed by a discrete step or a (substantially) continuous function, e.g. by a linear increase toward the center position of the organ and a linear decrease away from the center position of the organ.

For example, once the X-ray cone reaches the organ of interest, such as the heart, coverage and tube current may be increased. Larger coverage may be obtained by changing the collimation in a way that it is maximal when the X-ray source reaches the position corresponding to the center of the organ. A larger coverage, for a constant table feed, implies a relative pitch that is reduced. For example, assuming that coverage is large enough for covering the entire heart, data can be acquired such that a single heart beat cardiac reconstruction can be obtained. If coverage is not large enough, e.g. only parts of the heart are covered, the acquired data may still suffice for doing a multi-cycle cardiac reconstruction. Once sufficient data for the organ of interest are acquired, coverage and tube current may be reduced again, and the remaining body parts of interest can be scanned.

The device 10 may be adapted for controlling a table feed, e.g. a translation velocity, of the examination couch at a substantially constant value, e.g. maintaining the translation velocity constant, during the second operation. For example, the second operation may be a single helical scan, in which the table feed can be advantageously maintained constant. It is an advantage that motion artefacts due to acceleration and/or deceleration during the operation can be avoided. It is a further advantage that a risk to the subject implied by acceleration and/or deceleration can be reduced, e.g. in a trauma case. It is further advantage that the comfort for the subject can be increased by avoiding sudden and/or frequent changes in translation velocity. It is also an advantage that both an overview, e.g. a helical scan of a full body or a substantial part of a body, and a high temporal and/or spatial resolution scan of an organ of interest, e.g. a scan of the heart within a single heart beat, can be obtained in a single operation. References to a high temporal resolution refer to the acquisition of a detailed scan within a short period of time, e.g. such as to avoid or reduce motion artefacts, and do not imply that multiple volumetric images of the same volume are acquired for different points in time.

The device 10 may also comprise a further output 15 for controlling a contrast agent administration device 30, e.g. an automated contrast agent injector, for introducing a contrast agent in the body of the subject during the second operation. The processor may be adapted for sending a control signal via the further output 15 such as to administer the contrast agent to the subject when the translation of the subject by the automated examination couch causes the organ region to enter into the examination volume defined by the gantry, e.g. when the lower bound of the organ region coincides with the examination volume, or at a predetermined time before this position is reached such that the contrast agent can perfuse sufficiently the organ of interest.

In a second aspect, the present invention also relates to a multi-slice computed tomography system.

Referring again to FIG. 1, a multi-slice computed tomography system 1 in accordance with embodiments of the present invention is shown. The CT system 1 comprises a device 10, e.g. a console system, in accordance with embodiments of the first aspect of the present invention.

The CT system 1 is adapted for providing projection image data to the device 10, e.g. via the input 11 of the device 10.

The CT system 1 is adapted for receiving a control signal(s) from the device 10, e.g. via the output 12 of the device 10.

A CT system 1 in accordance with embodiments of the present invention may be adapted for performing one or more axial scans and/or one or more helical scans of a subject to be imaged, such as to generate radiographic projection data that can be reconstructed using a tomographic reconstruction algorithm. The CT system 1 is also adapted for acquiring a CT localizer radiograph of the subject, e.g. by translating the subject through an examination volume defined by the gantry while maintaining the X-ray source and detector in a stationary configuration.

For example, the CT system 1 may comprise a stationary gantry 202 and a rotating gantry 204, which may be rotatably supported by the stationary gantry 202. The rotating gantry 204 may rotate, about a longitudinal axis, around an examination volume 206 for containing at least part of the subject when acquiring the projection data. The CT system may comprise an automated examination couch 114 to support the subject in the examination volume 206.

The CT system 1 may comprise a radiation source 208, such as an X-ray tube, which may be supported by and configured to rotate with the rotating gantry 204. The radiation source may include an anode and a cathode. A source voltage applied across the anode and the cathode may accelerate electrons from the cathode to the anode. The electron flow may provide a current flow from the cathode to the anode, such as to produce radiation for traversing the examination volume 206.

The CT system 1 may comprise a detector array 210. This detector array may subtend an angular arc opposite the examination volume 206 relative to the radiation source 208. The detector array may include a two-dimensional array of pixels, e.g. comprising pixels adapted for transducing X-ray radiation incident thereon into a processable signal. The detector array may be adapted for detecting radiation traversing the examination volume and for generating a signal indicative of an energy thereof. The detector array may comprise a plurality of rows of detector pixels, arranged next to each other along the longitudinal axis. The number of rows may be sufficiently large to enable scans with a large coverage. The number of rows may be at least 128, preferably at least 256, e.g. 512 or 1024, or even larger. For example, 256 detector rows, in a typical configuration, may enable a coverage of 16 cm in the longitudinal direction in the examination volume.

The CT system 1 may comprise a controllable X-ray collimator 209 for changing a cone angle of the X-ray radiation emitted by the radiation source 208. For example, such collimator may comprise an X-ray radiation absorbing material, e.g. two such blocks of radiation absorbing material, in (e.g. in between) which an aperture is defined. An actuator may translate the radiation absorbing material to change the aperture area in response to a control signal. For example, the two blocks may be moved apart from each other or toward each other in response to a control signal. However, embodiments of the present invention are not limited to a specific construction of the controllable X-ray collimator, since various configurations of such controllable collimators are well-known in the art.

The CT system 1 may also comprise a contrast agent administration device 30, e.g. an automated contrast agent injector, for introducing a contrast agent in the body of the subject during the second operation. For example, the contrast agent administration device 30 may be operably connected to the further output 15 to administer the contrast agent to the subject upon receiving the control signal from the processor via the further output 15. In a third aspect, the present invention relates to a method for controlling a multi-slice computed tomography system, e.g. a multi-slice computed tomography system in accordance with embodiments of the second aspect of the present invention. The method may be executed by a device in accordance with embodiments of the first aspect of the present invention.

Figure 2:
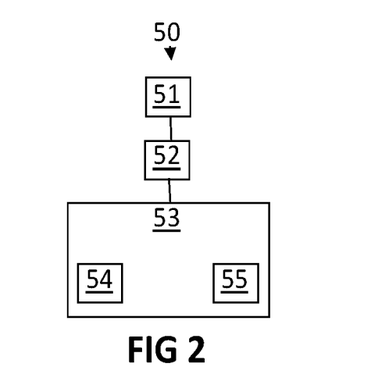
FIG. 2 illustrates a method in accordance with embodiments of the present invention.
Figure 3:
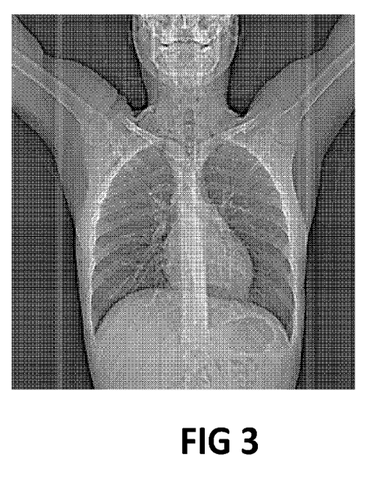
FIG. 3 shows an exemplary computed tomography localizer radiograph, to illustrate features of embodiments of the present invention.

Referring to FIG. 2, a method 50 in accordance with embodiments of the third aspect of the present invention comprises acquiring 51 a computed tomography localizer radiograph of a subject to be imaged using the multi-slice computed tomography system. The method 50 comprises defining 52, e.g. detecting, an organ region in the computed tomography localizer radiograph, in which the organ region substantially delimits an organ of interest, such as a heart, in the subject.

The organ region may be defined by a user, e.g. using a graphical user interface, or may be automatically detected.

Detecting the organ region may comprise fitting a model of the organ of interest, e.g. of a heart, on the computed tomography localizer radiograph, e.g. using a computer-implemented algorithm. The model may comprise a representative image of the organ and the step of fitting the model may comprise applying an image registration algorithm. The model may comprise a representative parametric model of the organ and the step of fitting may comprise estimating parameters of the model such as to conform with the computed tomography localizer radiograph. The model may be a two-dimensional model (e.g. a 2D representative image or a 2D parametric model) indicative of a projection view, of the organ of interest, that corresponds to the computed tomography localizer radiograph projection. The model may be a three-dimensional model (e.g. a 3D representative image or a 3D parametric model) of the organ of interest.

Detecting the organ region may comprise determining a lower bound, an upper bound and a center position of the organ of interest in a longitudinal direction corresponding to the direction of translation of the examination couch.

The method comprises acquiring 53 a helical computed tomography scan of the subject, in which the subject is translated by an automated examination couch through an examination volume.

Acquiring 53 the helical computed tomography scan may comprise controlling a translation velocity of the automated examination couch such as to remain substantially constant during the acquisition of the helical computed tomography scan.

The method comprises increasing an X-ray cone angle of the computed tomography system when the translation of the subject by the automated examination couch during the helical computed tomography scan causes the organ region to enter into an examination volume of the multi-slice computed tomography system and decreasing the X-ray cone angle when the translation of the subject during the helical computed tomography scan causes the organ region to leave the examination volume.

Increasing and decreasing the X-ray cone angle may comprise respectively enlarging and reducing an aperture of a controllable collimator of the multi-slice computed tomography system.

The X-ray cone angle may be increased when the upper bound of the organ region coincides with the examination region, and may be decreased when the lower bound of the organ region coincides with the examination region.

Increasing and decreasing the X-ray cone angle may be performed by a substantially continuous transition, e.g. increasing (for example) linearly from the upper bound to the center position of the organ and decreasing (for example) linearly from the center position of the organ to the lower bound.

The method 50 may also comprise increasing an X-ray tube current of the computed tomography system when the translation of the subject by the automated examination couch causes the organ region to enter into the examination volume and decreasing the X-ray tube current when the translation of the subject causes the organ region to leave the examination volume.

The method may also comprise controlling a contrast agent administration device to administer a contrast agent to the subject when, or at a predetermined time interval before, the translation of the subject by the automated examination couch causes the organ region to enter into the examination volume.

Figure 4:
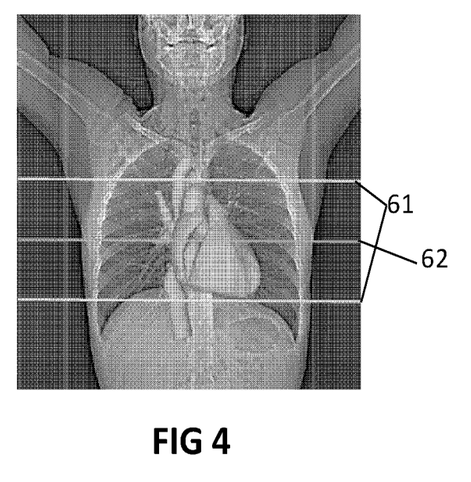
FIG. 4 shows a detected organ region in the exemplary computed tomography localizer radiograph, to illustrate features of embodiments of the present invention.

For example, the method may be applied for executing a scan in a trauma case, embodiments of the present application not being limited thereto. After acquiring the surview, the organ region is determined, e.g. the lower and upper bound of the heart in the longitudinal direction is determined. Referring to FIG. 4, an exemplary surview scan of a subject is shown. A 3D parametric model of the heart may then be registered with the surview scan, as illustrated in FIG. 4. The cranial and caudal edges of the heart 61 can thus be determined, as well as a center line 62. Then, the helical scan may be performed. This acquisition may start, for example, with a collimation corresponding to a reduced coverage, such as a coverage of 4 cm (e.g. in which only 64 detector rows are irradiated by the X-ray source). This could, for example, correspond to a relative pitch in the order of 1. Upon reaching the position of the cranial edge (for example), the pitch may be reduced by increasing the aperture of the collimation, e.g. such as to correspond to a full coverage. This increase may be gradually increasing toward the center line, and may decrease back to the original collimation corresponding to the reduced coverage when reaching the caudal edge (for example).

The invention claimed is:

1. A device for controlling an image acquisition of a multi-slice computed tomography system comprising a rotatable gantry, a multi-row detector, an X-ray source and an automated examination couch moving in a longitudinal direction, the device comprising:
   an input for receiving projection image data from the multi-row detector of the multi-slice computed tomography system;
   an output for controlling operation of the multi-slice computed tomography system; and
   a processor configured to control a first operation of the multi-slice computed tomography system via the output so that a computed tomography localizer radiograph of a subject to be imaged is acquired,
   wherein the processor is adapted for receiving the computed tomography localizer radiograph via the input,
   wherein the processor is adapted for controlling a second operation of the computed tomography system via the output so that a large volume overview that comprises at least an organ region defined on the computed tomography localizer radiograph and substantially delimiting an organ of interest in the subject is acquired, in which the subject is translated by the automated examination couch through an examination volume,
   wherein controlling the second operation comprises increasing an X-ray cone angle of the computed tomography system in the longitudinal direction when the translation of the subject by the automated examination couch causes the organ region to enter into the examination volume and decreasing the X-ray cone angle when the translation of the subject causes the organ region to leave the examination volume.

2. The device of claim 1, wherein the processor is adapted for controlling an aperture of a controllable collimator of the computed tomography system to increase and decrease said X-ray cone angle.

3. The device of claim 1, wherein the processor is adapted for detecting the organ region in the computed tomography localizer radiograph.

4. The device of claim 3, wherein the processor is adapted for fitting a model of the organ of interest on the computed tomography localizer radiograph.

5. The device of claim 4, wherein the model comprises a representative image of the organ and the fitting comprises applying an image registration algorithm, or wherein the model comprises a representative parametric model of the organ and the fitting comprises estimating parameters of the model such as to conform with the computed tomography localizer radiograph.

6. The device of claim 4, wherein the model is a two-dimensional model indicative of a projection view of the organ of interest that corresponds to the computed tomography localizer radiograph, or wherein the model is a three-dimensional model of the organ of interest.

7. The device of claim 1, wherein the processor is adapted for defining the organ region by a lower bound, an upper bound and a center position of the organ in a longitudinal direction corresponding to the direction of translation of the examination couch.

8. The device of claim 7, wherein the processor is adapted for increasing the X-ray cone angle when the upper bound of the organ region coincides with the examination region, and decreasing the X-ray cone angle when the lower bound of the organ region coincides with the examination region.

9. The device of claim 8, wherein the processor is adapted for increasing and decreasing the X-ray cone angle by a substantially continuous transition.

10. The device of claim 1, wherein controlling the second operation comprises increasing an X-ray tube current of the computed tomography system when the translation of the subject by the automated examination couch causes the organ region to enter into the examination volume and decreasing the X-ray tube current when the translation of the subject causes the organ region to leave the examination volume.

11. The device of claim 1, wherein the processor is adapted for controlling a translation velocity of the automated examination couch such as to remain substantially constant during the second operation.

12. The device of claim 1, wherein the device is an operator console system for controlling the multi-slice computed tomography system.

13. The device of claim 1, further comprising a further output for controlling a contrast agent administration device for introducing a contrast agent in the body of the subject, and wherein the processor is adapted for sending a control signal via the further output to administer the contrast agent to the subject when, or at a predetermined time interval before, the translation of the subject by the automated examination couch causes the organ region to enter into the examination volume.

14. A multi-slice computed tomography system comprising a device in accordance with claim 1.

15. A method for controlling a multi-slice computed tomography system comprising an X-ray source, a multi-row detector and an automated examination couch moving in a longitudinal direction, the method comprising:
   acquiring a large volume computed tomography localizer radiograph of a subject to be imaged using the multi-slice computed tomography system;
   defining an organ region in the large volume computed tomography localizer radiograph having the organ region substantially delimiting an organ of interest in the subject;
   acquiring a large volume overview that comprises at least the organ region via a helical computed tomography scan of the subject having the subject being translated by the automated examination couch through an examination volume; and
   increasing an X-ray cone angle of the computed tomography system in the longitudinal direction when the translation of the subject by the automated examination couch during the helical computed tomography scan causes the organ region to enter into the examination volume of the multi-slice computed tomography system and decreasing the X-ray cone angle in the longitudinal direction when the translation of the subject during the helical computed tomography scan causes the organ region to leave the examination volume.

* * * * *